US00PP37156P2

(12) United States Plant Patent
Hansen

(10) Patent No.: US PP37,156 P2
(45) Date of Patent: Dec. 16, 2025

(54) ***BAPTISIA* PLANT NAMED 'Golden Anniversary'**

(50) Latin Name: ***Baptisia* hybrid**
Varietal Denomination: Golden Anniversary

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,462

(22) Filed: Jan. 29, 2025

(51) Int. Cl.
*A01H 6/00* (2018.01)
*A01H 5/02* (2018.01)
*A01H 5/12* (2018.01)

(52) U.S. Cl.
USPC ..... Plt./263.1
CPC ..... *A01H 6/00* (2018.05); *A01H 5/02* (2013.01); *A01H 5/12* (2013.01)

(58) Field of Classification Search
USPC ..... Plt./263.1
CPC ..... A01H 6/00; A01H 5/02
See application file for complete search history.

*Primary Examiner* — Keith O. Robinson

(57) ABSTRACT

A new and distinct cultivar of hardy herbaceous False Indigo plant named 'Golden Anniversary' characterized by flowers of deep indigo beginning in late May and continuing for two to three weeks. The new plant has a rounded mounded shaped, multi-stemmed, winter-hardy habit with glaucous golden-yellowish tri-foliate foliage that compliment the flowers. The new plant is suitable for landscaping as a specimen or en masse.

2 Drawing Sheets

Botanical classification: *Baptisia* hybrid.
Cultivar designation: 'Golden Anniversary'.

STATEMENT REGARDING PRIOR DISCLOSURES UNDER 37 CFR 1.77(B)(6)

The first offer for sale and sale of *Baptisia* 'Golden Anniversary' was by Walters Gardens, Inc. on Feb. 1, 2024. Information and plants for this sale and all sales thereafter were obtained from the inventor. No plants of *Baptisia* 'Golden Anniversary' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Golden Anniversary' and will be referred to hereafter by its cultivar name, 'Golden Anniversary', and the new plant. The new plant represents a new False Indigo, a hardy herbaceous perennial grown for landscape and cut flower use.

'Golden Anniversary' arose from an ongoing breeding program of the inventor at a wholesale perennial nursery in Zeeland, Michigan with evaluation for the specific intention of improving garden worthiness of perennial false indigo plants with a wider variety of flower colors and improved garden habit.

*Baptisia* 'Golden Anniversary' was a single seedling selection from a cross between 'Dark Chocolate' U.S. Plant Pat. No. 30,959 as the female or seed parent times 'Dutch Chocolate' U.S. Plant Pat. No. 23,872 as the male or pollen parent in the spring of 2015 at a wholesale perennial nursery in Zeeland, Michigan. Seeds were collected from the individual selected female plant on Jul. 15, 2015. The seeds were sown at the same nursery in the fall of 2015 and the initial selection was made in the spring of 2017 at the same nursery and given the breeder code 15-2-4.

'Golden Anniversary' was initially asexually propagated by stem cuttings at a wholesale perennial nursery in Zeeland, Michigan in 2018. The resultant plants have demonstrated that the new plant has remained stable and true to type in successive generations of asexual propagation.

'Blueberry Sundae' has a similar habit and flowers, but the foliage is deep blue-green. 'Sparkling Sapphires' is shorter and broader in habit with intense blue flowers and grayish-green foliage. 'Indigo Spires' has a larger habit with dark indigo flowers and dark green foliage. 'White Gold' has creamy white flowers on smaller inflorescences. No other cultivar of *Baptisia* known to the inventor has violet flowers with golden chartreuse foliage through the flowering season.

The female parent is larger in habit and has chocolate-purple flowers and medium green foliage. The male parent has a smaller habit, the flowers are chocolatey-purple and the foliage is deep bluish-green.

The new plant differs from all *Baptisia* known to the inventor in the following combined traits:

1. Numerous flowers occur on long spikes;
2. Bright-yellowish, tri-foliate foliage through the growing season until frost;
3. Flowers area deep indigo and compliment the foliage;
4. Flowering begins about late-May in Michigan and continues for two to three weeks;
5. Rounded mound shaped, multi-stemmed, winter-hardy habit.

BRIEF DESCRIPTION OF THE DRAWINGS

The photographs of 'Golden Anniversary' demonstrate the unique traits of the new plant and the overall appearance.

The colors are as accurate as reasonably possible with color reproductions. Variation in ambient light spectrum, source and direction may cause the appearance of minor variation in color. The accompanying photograph is of an eight-year-old plant growing in an open full-sun trial garden in Zeeland, Michigan.

DETAILED BOTANICAL DESCRIPTION OF THE PLANT

Figure 1:
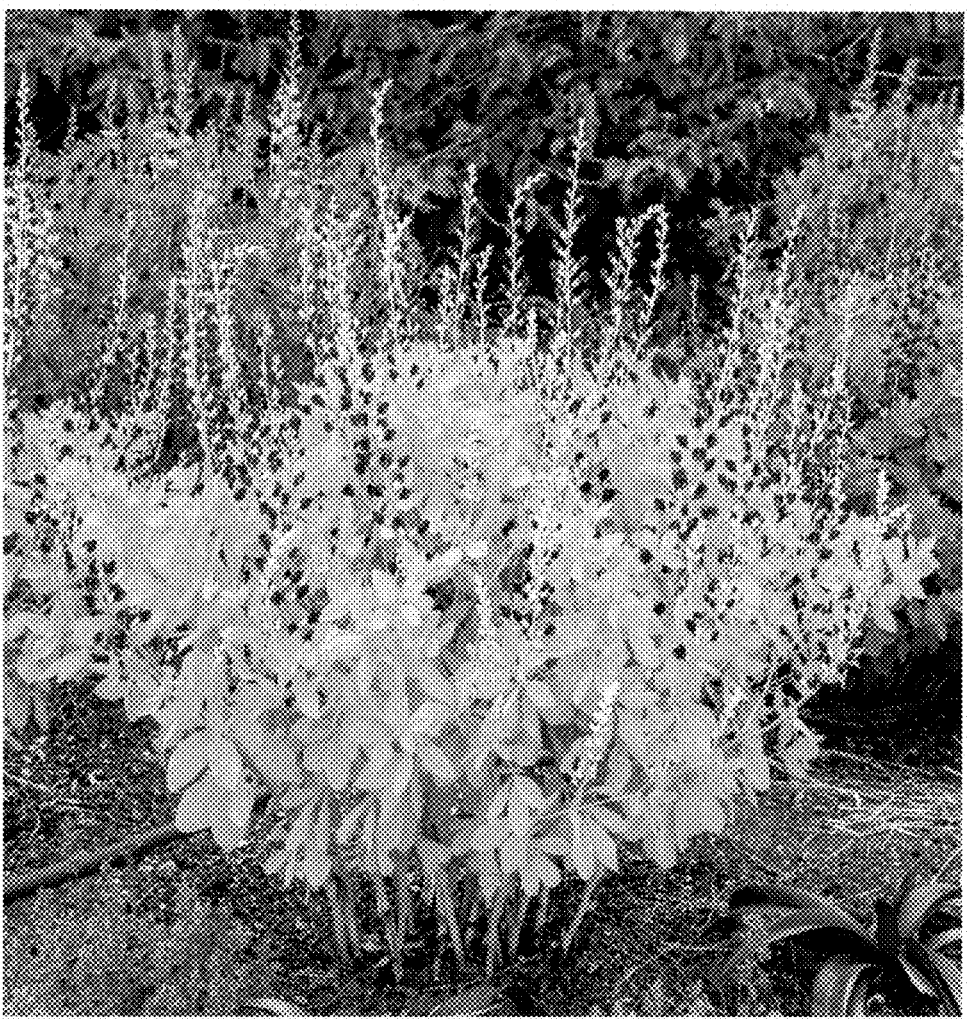
FIG. 1 shows the habit of a plant in full flower.
Figure 2:
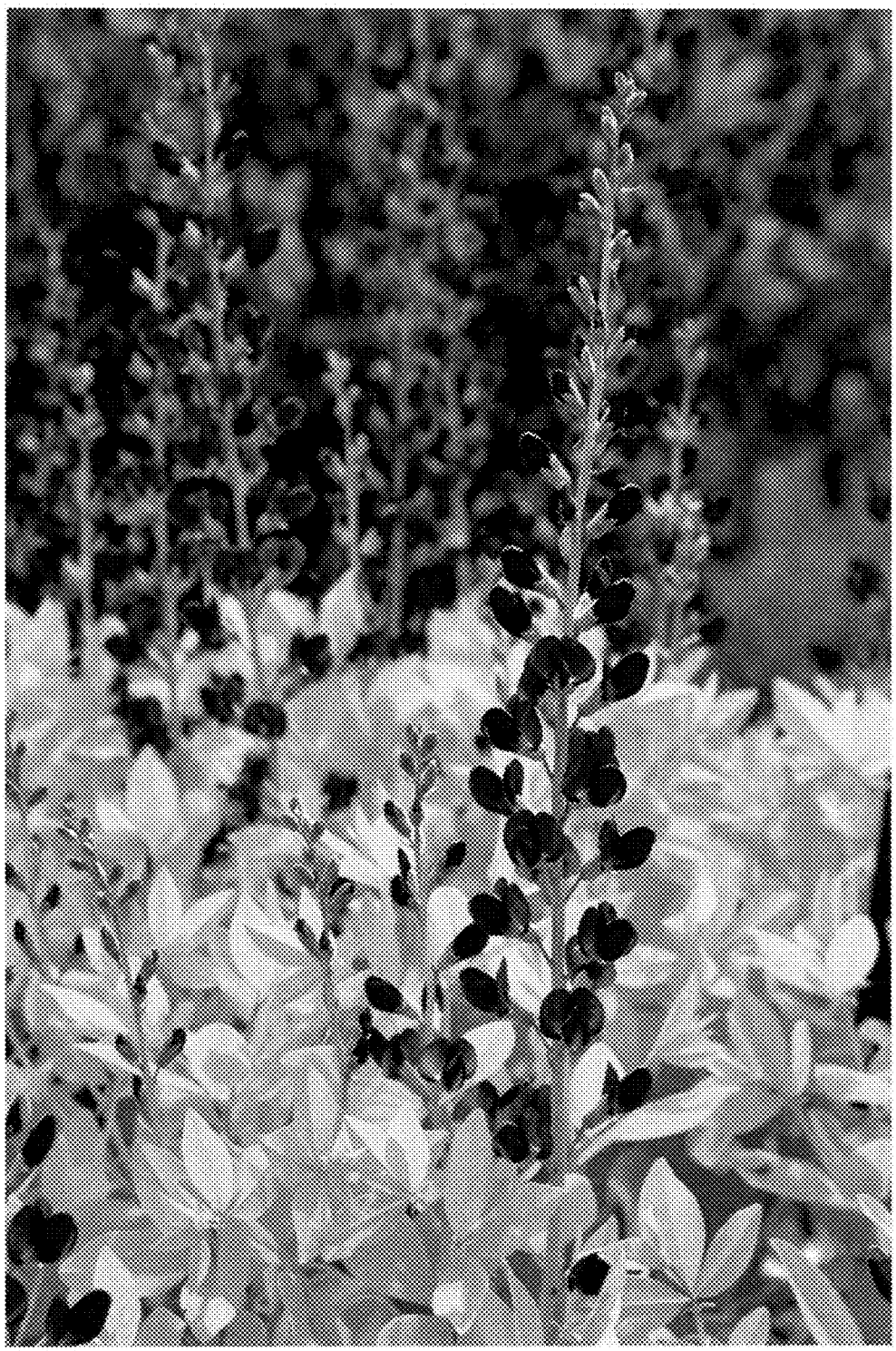
FIG. 2 shows a close-up of the inflorescence with golden-yellowish foliage.

The following is a detailed description an eight-year-old plant of 'Golden Anniversary' as grown outdoors in a trial block at a wholesale perennial nursery in Zeeland, Michigan. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, initially vase-shaped growth habit develops into rounded mound later in the season, with long inflorescences held above the foliage;

Plant size: Stems and crown about 30 cm across at soil level, foliage at flowering about 76 cm tall from soil to top of foliage; at maturity plant foliage height about 97 cm wide about 50 cm above soil; flowering to about 90 cm tall and about 124 cm wide;

Roots: Fibrous, well-branched, long, deeply rooted;

Root color: Nearest RHS 161D;

Propagation method: Stem cuttings, rooting in' about three weeks;

Growth rate: Moderate to average;

Stems: Rigid and upright; highly glaucous; glabrous; cylindrical with shallow longitudinal furrows; lower two to four nodes without leaves or branches; normally two to three branches per plant below flowers; about 31stems per clump;

Stem size: Main stem to about 9 mm diameter at base and 97 cm tall, average about 82 cm long and about 7 mm diameter; to about 58 cm long from soil to below initial flowers;

Stem branches: Primary branches at 45 to 60-degree angle above horizontal, up to 64 cm long and 5 mm diameter, average for primary branches about 28 cm long and 4 mm diameter, smaller distally; and three to six alternate secondary branches per stem of about 22 cm long and 3 mm diameter, averaging about 15 cm long and 3 mm diameter;

Stem color: Between RHS 145A and RHS 146D;

Stem scales: At stem nodes; lanceolate; emarginate to retuse apex with sharply pointed sides; truncate clasping base; margin entire; dehiscing to leave behind thin scar on stem; about 18 mm long and 2 mm wide in center of apex; about 19 mm wide at base and 22 mm wide in center;

Stem scale color: Between RHS 145A and RHS 146D;

Nodes: Up to 8 cm apart between lowest branches, average internode separation about 6 cm;

Node color: Variable, nearest RHS 139D, RHS 148D and nearest RHS N186A;

Foliage: Alternate; ternate to palmately compound with three leaflets; outer two leaflets independent, at nearly 90-degree angle to middle leaflet; up to 7 cm long and 13 cm wide;

Leaflet: Three; oblanceolate; apex rounded; base cuneate; margins entire; petiolate; adaxial and abaxial surfaces matte, glabrous, and non-glaucous; middle lobe to about 6.8 cm long and 3.2 cm wide, side lobes about 6.3 cm long and 3 cm wide;

Leaflet color: Newly expanding adaxial variable, nearest RHS N144A and between RHS 146D and RHS N144A, abaxial variable nearest RHS N144A and RHS 146D; mature adaxial variable, nearest RHS 151D. nearest RHS 145A, and between RHS 151D and RHS N144A, abaxial between RHS 145A and RHS 146D;

Venation: Pinnate; glabrous; thin; more conspicuous on mature foliage; abaxial midrib glaucous becoming lustrous;

Vein color: Newly expanding foliage adaxial midrib and primary veins between RHS 151D and RHS 147C; newly expanding abaxial midrib and primary veins between RHS 146D and RHS N144A; mature adaxial midrib and secondary veins nearest RHS N148C; mature abaxial midrib between RHS 145C and RHS 146D and secondary veins nearest RHS 146D;

Petioles: Glabrescent; slightly glaucous; slightly concavo-convex; to about 4 mm long and 2 mm wide at base, average 3 cm long and 1.5 mm wide;

Petiole color: Adaxial center nearest RHS N144A when young and maturing to nearest RHS N144D;

Stipules: Narrowly lanceolate, narrowly acute apex with base truncate; to about 12 mm long and 3 mm wide, average 6 mm long and 2 mm wide with largest stipules below primary branches and decreasing distally and on secondary branches to about 3 mm long and 0.5 mm wide;

Stipule color: Between RHS 144A and RHS 145A both surfaces;

Peduncle: Cylindrical with vertical shallow ridges; glaucous; glabrous; with about 50 flowers, length from first flower to apex about 50 cm; diameter at the base of first flower about 6 mm and about 2 mm diameter at the apex;

Peduncle color: Between RHS 145A and RHS 146D;

Pedicel: Cylindrical, glabrous, glaucous; about 4 mm long and 1 mm diameter;

Pedicel color: Nearest RHS 146C with slight blush of nearest RHS N92A;

Calyx: Campanulate; five-lobed; to about 9 mm long, 7 mm tall, and 8 mm across at apex;

Sepals: Five; two fused dorsal sepals, one ventral and two lower lateral; acute apices; fused into tube in proximal 6 mm; margin entire; glabrous adaxial and abaxial; fused dorsal sepals to about 9 mm long and 5 mm wide at fusion; other three sepals to about 9 mm long and 3 mm across at fusion;

Sepal color: Adaxial nearest RHS 145C; abaxial between RHS 146D and RHS N144A with light tinting of nearest RHS N92A dorsally;

Buds one day prior to anthesis: Oblong-elliptic, flatted vertically; to about 23 mm long and 10 mm tall and 7 mm wide, slightly larger in proximal flowers;

Bud color one day prior to anthesis: Exposed keel petal ventrally nearest RHS 4C and distally exposed portion nearest RHS 4C with a moderate blush of nearest RHS N92D; enfolded banner petal dorsal portion nearest RHS N92A, center and side portion nearest RHS 92D; exposed alae petals nearest RHS N92D;

Flower: Zygomorphic, papilionaceous, non-secund, held at about a 45-degree angle above horizontal; to about 48 flowers per main raceme and about 17 per secondary branch; seasonally effective for two and a half to three weeks beginning in late May in Zeeland, MI; individually to about 25 mm long, 14 mm tall and 17 mm wide at largest portions; consisting of an upper banner, a lower keel made up of two lobes folded around gynoecium and androecium; and two lateral wings or alae laterally appressed against keel;

Lasting: Individual flowers remain effective as cut flowers and on raceme for about four days; Flower fragrance: none detected;

Petals: Five; with a lower fused keel, an upper banner, and two lateral wings or alae; keel comprised of two sections united along the ventral edge and folded around stamens and pistil;

*Banner petal*.—Reflexed upward and backward and pinched in the middle; apex retuse, base claw-like, margin entire; to about 18 mm long, 16 mm across natural width, 20 mm wide flattened spread and 13 mm tall; with rounded emarginate apex notched about 2 mm deep; basal portion attenuate claw-type, 5 mm long and 1.5 mm wide at base.

*Banner color*.—Upon first opening-adaxial distal and margin nearest RHS N92D, center nearest RHS N92A, with base and claw nearest RHS 145C; abaxial center nearest RHS N92A, distally and laterally nearest RHS N92D with basal blade and claw nearest RHS 145C; mature adaxial and abaxial colors remaining unchanged.

*Alae*.—Two; papilionaceous corolla appendage with rounded apex and claw-like base; with a 2 mm long by 2 mm wide lobe pointing toward base and about one-third of the way from base; about 20 mm long, and 8 mm tall, with the claw to 2 mm wide at base of blade and 1.5 mm wide at base and 5 mm long; blade about 17 mm long and 8 mm wide.

*Alae color*.—Upon first opening-adaxial and abaxial ventral portion nearest RHS 4C, center and dorsal portion adaxial and abaxial nearest RHS 4D and adaxial and abaxial claw, lobes, and blade base between RHS NN155A and RHS 11D; abaxial distal 2 mm moderately blushed with nearest RHS N92D; mature adaxial and abaxial between RHS 11D and RHS NN155A, with adaxial blade moderately blushed with nearest RHS N92D in apical two-thirds, mature abaxial moderately to lightly blushed in apical two-thirds of blade to nearest RHS N92D;

*Keel*.—Comprised of two main lobes that are folded around stamens and pistil; united along ventral margin in the distal one-third with the apex emarginate or retuse and the bases separate and claw-like; margin entire; top edge about one-third of the way from base has 2 mm smaller lobe pointing toward base; about 23 mm long and 10 mm tall; blade portion to about 17 mm long and 9 mm tall, with claw to about 5 mm long and base narrowed to 1.5 mm wide at base.

*Keel color*.—Upon first opening-adaxial small lobe and proximal nearest RHS NN155A, center and distal blade nearest RHS 90A, and claw nearest RHS 145D; abaxial small lobe and basal portion nearest RHS NN155A, center and distal blade nearest RHS N92D, and claw nearest RHS 145D; mature adaxial and abaxial colors unchanged.

Receptacle: Disk-shaped, about 4 mm diameter and 3 mm depth; color between RHS 146D and RHS 147C with light blush of nearest RHS N92A;

Gynoecium: One, with superior ovary and stipe; to about 21 mm long;

*Style*.—Cylindrical; glabrous; slightly glaucous; tapered and curved upwardly distally, about 11 mm long and about 0.7 mm diameter above ovary; color nearest RHS 145C.

*Stigma*.—About 0.2 mm diameter; color nearest RHS NN155A.

*Ovary*.—Superior above hypanthium, suspended by stipe; about 5 mm long and about 1.5 mm in diameter; color between RHS 145A and RHS 145B.

*Stipe*.—Cylindrical; glabrous; slightly lustrous; about 3 mm long and 0.7 mm diameter; color nearest RHS 145B with slight blush of nearest RHS N92A.

Androecium:

*Stamens*.—Ten.

*Filament*.—Glabrous; slightly lustrous; not united 20 mm in length and about 0.5 mm in diameter; slightly curved upwardly distally; color nearest RHS 145D.

*Anther*.—Dorsifixed, oblong; about 1.7 mm long and 1.2 mm wide; color nearest RHS 17A.

*Pollen*.—Spherical; abundant; color nearest RHS 17A.

Fruit: Bivalve inflated ellipsoidal pod; glabrous; about 27 mm long, 12 mm across and 10 mm thick; with thin, linear, arcuate, terminal beak about 6 mm long and about 1 mm diameter at base; rounded base;

Fruit color: At maturity mottled with nearest 200A and between RHS 165B and RHS 199B;

Seeds: About 12 to 14 per pod (open pollinated); reniform; glabrous; about 4 mm long, 3 mm across and 2 mm thick; color nearest RHS 200B;

Hardiness: To USDA zones 4 to 9; able to withstand drought conditions once established;

Growth: Tolerant of heavy clay or light loamy-sand soils;

Diseases: Susceptibility or resistance to diseases beyond that typically found in other false indigo plants has not been observed, including *Odocoileus, Sylvilagus, Cylindrocladium, Erysiphe*, and *Puccinia* sp.

It is claimed:

1. A new and distinct cultivar of *Baptisia* plant named 'Golden Anniversary' as herein described and illustrated.

* * * * *